United States Patent
Herbst et al.

(10) Patent No.: US 11,432,787 B2
(45) Date of Patent: Sep. 6, 2022

(54) METHOD AND APPARATUS FOR IMAGE NOISE REDUCTION

(71) Applicant: Siemens Healthcare GmbH, Erlangen (DE)

(72) Inventors: Magdalena Herbst, Erlangen (DE); Steffen Kappler, Effeltrich (DE); Ludwig Ritschl, Buttenheim (DE)

(73) Assignee: Siemens Healthcare GMBH, Erlangen (DE)

( * ) Notice: Subject to any disclaimer, the term of this patent is extended or adjusted under 35 U.S.C. 154(b) by 0 days.

(21) Appl. No.: 17/480,243

(22) Filed: Sep. 21, 2021

(65) Prior Publication Data

US 2022/0096034 A1 Mar. 31, 2022

(30) Foreign Application Priority Data

Sep. 25, 2020 (DE) ...................... 10 2020 212 089.7

(51) Int. Cl.
*A61B 6/00* (2006.01)
*A61B 6/03* (2006.01)
*A61B 6/02* (2006.01)

(52) U.S. Cl.
CPC ............ *A61B 6/5258* (2013.01); *A61B 6/025* (2013.01); *A61B 6/032* (2013.01); *A61B 6/487* (2013.01); *A61B 6/502* (2013.01)

(58) Field of Classification Search
CPC ....... A61B 6/5258; A61B 6/025; A61B 6/032; A61B 6/487; A61B 6/502; G06V 10/30;
(Continued)

(56) References Cited

U.S. PATENT DOCUMENTS

| 6,310,967 B1 | 10/2001 | Heine et al. |
| 2004/0258325 A1* | 12/2004 | Sasada ................... G06T 5/004 382/275 |

(Continued)

FOREIGN PATENT DOCUMENTS

DE 102009039987 A1 3/2011

OTHER PUBLICATIONS

Dabov, K., Foi, A., Katkovnik, V., and Egiazarian, K., "Image denoising by sparse 3-D transform-domain collaborative filtering", IEEE transactions on image processing 16, 2080-95 (Aug. 2007).

(Continued)

*Primary Examiner* — Courtney D Thomas
(74) *Attorney, Agent, or Firm* — Harness, Dickey & Pierce, P.L.C.

(57) ABSTRACT

A method and a system are for image noise reduction. In an embodiment, the method includes producing a recorded image; establishing an amount of noise of the recorded image; decomposing the amount of noise into a number of N frequency-dependent noise components for N frequency bands, the number of N frequency-dependent noise components including respective data points respectively reproducing noise, of the amount of noise in the recorded image, for the respective frequency bands of the N frequency bands; examining the number of N frequency-dependent noise components for outlier data points, where an intensity lies outside a range of values, and forming moderated noise components by moderation of values of the outlier data points established in the examining of the number of N frequency-dependent noise components; and subtracting the moderated noise components from the recorded image.

29 Claims, 6 Drawing Sheets

(58) Field of Classification Search
CPC ...... G06V 2201/03; G06T 2207/10081; G06T 2207/20016; G06T 2207/20056; G06T 2207/20064; G06T 2207/30004; G06T 5/004; G06T 5/10; G06T 7/40
See application file for complete search history.

(56) References Cited

U.S. PATENT DOCUMENTS

| | | |
|---|---|---|
| 2011/0052030 A1 | 3/2011 | Bruder et al. |
| 2019/0287220 A1 | 9/2019 | Srivastava et al. |
| 2020/0163638 A1 | 5/2020 | Wicklein et al. |

OTHER PUBLICATIONS

Eckert, Dominik et al: "Deep learning-based denoising of mammographic images using physics-driven data augmentation"; Bildverarbeitung für die Medizin 2020; Springer Vieweg; Wiesbaden; 2020; pp. 94-100.

Zhang, Kai et al: "Beyond a gaussian denoiser: Residual learning of deep cnn for image denoising"; IEEE transactions on image processing; 2017; vol. 26; No. 7; pp. 3142-3155.

German Office Action for German Patent Application No. 102020212089.7 dated May 14, 2021.

German National Receipt of Grant for German Patent Application No. 102020212089.7 dated Jun. 7, 2021.

\* cited by examiner

METHOD AND APPARATUS FOR IMAGE NOISE REDUCTION

PRIORITY STATEMENT

The present application hereby claims priority under 35 U.S.C. § 119 to German patent application number DE102020212089.7 filed Sep. 25, 2020, the entire contents of which are hereby incorporated herein by reference.

FIELD

Example embodiments of the invention generally relate to a method and an apparatus for image noise reduction, in particular of x-ray images, preferably for statistically motivated, frequency-based backup of image noise reduction algorithms.

BACKGROUND

When images are recorded, noise, which can become noticeable as disturbing to a greater or lesser extent, is always contained in the images. If these images are to be evaluated, e.g. in an examination of medical images by a doctor, a large noise component is very disadvantageous. Therefore the noise in recorded images is often reduced before an examination by image noise reduction methods, which are based for example on classical non-linear filters, iterative methods or specifically on artificial intelligence AI.

A known risk that has long existed in the development and application of image noise reduction algorithms is the unintentional removal of information relevant to the image, which can occur as a negative side effect during the reduction of noise in image data. A further risk is that available structures are disproportionately processed out or entirely new structures are even incorrectly inserted. The last point above all relates to algorithms with AI, since these have been trained with a large but finite volume of data and thus are not prepared for every scenario.

Depending on the method chosen for noise reduction and the desired level of noise reduction, this risk is low, slight or high. With medical image data in particular subtle structures can influence the appraisal, so that it must therefore be insured that on the one hand these must be preserved, but they must not be additionally emphasized.

Conventional noise reduction methods, i.e. methods without AI, either have parameters with which the algorithm can be set according to the application, or reduce noise according to a statistic of the data (e.g. BM3D or an iterative CT image filter for noise reduction, known as "IRIS" for short). In relation to the "BM3D" method, the reader is referred to K. Dabov, A. Foi, V. Katkovnik, and K. Egiazarian "Image denoising by sparse 3d transformdomain collaborative filtering" (IEEE Transactions on Image Processing, 16(8): 2080-2095, August 2007). In relation to "IRIS" filters to US 2011/0052030 A1 or DE102009039987A1, the corresponding German application. With IRIS for example a decision is made for each image point based on the local statistic as to whether this involves a noise pixel, which is to be smoothed, or structure, which is to be preserved.

SUMMARY

The inventors have discovered that a disadvantage of the known methods is that the risk portrayed above that structures in images will be incorrectly deleted, processed out or created.

At least one embodiment of the present invention specifies an alternate, more convenient method and/or a corresponding apparatus for image noise reduction, in particular of x-ray images, with which at least one of the disadvantages described above will be reduced or even avoided.

Embodiments are directed to a method, an apparatus, a control facility and an imaging system.

At least one embodiment of the inventive method for image noise reduction, in particular of x-ray images, comprises:

production of a recorded image;

establishing of an amount of noise of the recorded image;

decomposition of the amount of noise into a defined number of N frequency-dependent noise components for N frequency bands, wherein the noise components comprise data points, which reflect the noise in the recorded image for the frequency band concerned;

examination of the noise components (for a number of their image points/all image points) for (statistical) outlier image points of which the intensity lies outside a predetermined range of values and formation of moderate noise components by moderation of the values of the outlier image points established in the examination; and subtraction of the moderated noise components from the recorded image.

An inventive apparatus for image noise reduction of an embodiment comprises:

An (in particular medical) imaging system designed to produce a recorded image or a data interface for receiving a recorded image, e.g. a radiography system, mammography system (also tomosynthesis), fluoroscopy system or a computed tomography system, A noise reduction unit designed to establish an amount of noise of the recorded image, A decomposition unit designed to decompose the amount of noise into a predetermined number of N frequency-band-dependent noise components for N frequency bands, wherein the noise components comprise data points, which reproduce the noise at points in the recorded image for the frequency band concerned, A moderation unit designed to examine the noise components for outlier data points, the intensity of which lies outside a predetermined range of values and for formation of moderated noise components by moderation of the value of the outlier data points established in the noise components in the examination, Optionally a combination unit, which is designed to combine the moderated noise components into a moderated amount of noise, (before these are subtracted from the recorded image by the subsequent subtraction unit), and A subtraction unit designed to subtract the moderated noise components from the recorded image.

An inventive control facility of an embodiment for control of an imaging system, in particular a medical imaging system (in particular for x-ray images), preferably a radiography system, fluoroscopy system, mammography system or a computed tomography system, is designed for carrying out an embodiment of an inventive method and/or comprises an embodiment of an inventive apparatus.

An inventive imaging system of an embodiment, in particular a medical imaging system, preferably a radiography system, fluoroscopy system, mammography system or a computed tomography system, comprises an embodiment of an inventive control facility.

A method for image noise reduction of an embodiment, comprises:

producing a recorded image;

establishing an amount of noise of the recorded image;

decomposing the amount of noise into a number of N frequency-dependent noise components for N frequency bands, the number of N frequency-dependent noise components including respective data points respectively reproducing noise, of the amount of noise in the recorded image, for the respective frequency bands of the N frequency bands;

examining the number of N frequency-dependent noise components for outlier data points, where an intensity lies outside a range of values, and forming moderated noise components by moderation of values of the outlier data points established in the examining of the number of N frequency-dependent noise components; and subtracting the moderated noise components from the recorded image.

An apparatus for image noise reduction of an embodiment, comprises:

at least one of an imaging system designed to produce a recorded image and a data interface to receive a recorded image;

a noise reduction unit to establish an amount of noise of the recorded image;

a decomposition unit to decompose the amount of noise into a number of N frequency-dependent noise components for N frequency bands, the number of N frequency-dependent noise components including respective data points respectively reproducing noise, of the amount of noise in the recorded image, at respective points of the recorded image for respective frequency bands of the N frequency bands;

a moderation unit to examine the number of N frequency-dependent noise components for outlier data points, where an intensity lies outside a range of values, and to form moderated noise components by moderation of values of the outlier data points established in the examining of the number of N frequency-dependent noise; and a subtraction unit to subtract the moderated noise components from the recorded image.

A control facility for controlling an imaging system of an embodiment, comprises, the apparatus of an embodiment.

An imaging system of an embodiment, comprises, the control facility of an embodiment.

A non-transitory computer program product of an embodiment stores a computer program, directly loadable into a memory facility of a control facility, including program sections for carrying out the method of an embodiment when the computer program is executed in the control facility.

A non-transitory computer-readable medium of an embodiment stores program sections readable in and executable by a processor, to carry out the method of an embodiment when the program sections are executed by the processor.

BRIEF DESCRIPTION OF THE DRAWINGS

The invention will be explained once again below with reference to the enclosed figures with the aid of example embodiments. In this explanation the same components are labeled in the various figures with the same reference numbers. The figures are as a rule not true-to-scale. In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++,C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for image noise reduction, in particular of x-ray images, comprises:

Production of a recorded image.

The recorded image is recorded in this case by a radiology device or by a computed tomograph and inevitably contains noise. It should be noted that the following steps can be applied to reconstructed images or to raw data. Therefore a reconstructed image and also raw data of an image can be understood as a recorded image. Any given number of processing steps can also have been applied however. Likewise further processing steps can be applied after the method. For example the reconstruction of tomosynthesis recordings or the creation of synthetic 2D images from the tomosynthesis recordings. The method is preferably applied to raw data, since in the data the statistical characteristics of the noise are known or can be measured. Raw data can be detector intensity values for example, for which detector-dependent corrections can also have been applied, such as for example the correction of defective pixels. Preferably however further processing steps such as for example scattered radiation correction, contrast adaptation, edge reinforcement have not yet been applied during image recording. The recorded image can also involve transformed raw data. For example it can be helpful to apply an Anscombe transformation to the raw data. With this step Poisson noise is converted into white noise (Gaussian noise with a standard deviation of one). This allows the characteristics of the noise to be better described. If CT data is used it should be noted that the characteristics of the noise can depend additionally for example on the reconstruction kernel used.

Establishing of an amount of noise of the recorded image.

This amount of noise is established via methods for image analysis. Suitable methods are known to the person skilled in the art. Basically it is of no importance for the method which method is applied, provided an amount of noise is established, wherein naturally the quality of the result (the denoised image) depends on the quality of the amount of noise established. The inventive method serves in this case to improve a given noise reduction method. Known (and preferred) image noise reduction algorithms are the above-mentioned methods BM3D, IRIS (iterative CT image filters for noise reduction) or methods that establish the amount of noise with AI. The entire image in this case is divided into a noise component and a component of image-relevant information, wherein the latter does not absolutely have to be established but can serve to improve the noise reduction algorithm.

Up to this point the method corresponds to the prior art, in which the component of the image is considered that was recognized by the algorithm as noise, and is then deducted from the original image in order to obtain the noise-free or noise-reduced image. The improvement as claimed in the invention is now produced by the following steps.

Decomposition of the amount of noise into a defined number of N frequency-dependent noise components for N frequency bands, wherein the noise components comprise data points, which reflect the noise in the recorded image for the frequency band concerned.

A frequency-based decomposition of recorded images is well known in the prior art. An example of this is a two-dimensional Fourier decomposition, in particular a Fast-Fourier transformation, or a wavelet transformation. Since the amount of noise corresponds by its nature to a recorded image (either an image or raw data of an image which represents the noise), a frequency-based decomposition of the amount of noise is thus possible. Unsharpnesses and sharpnesses, for which the information can be found in frequency bands, belong to the characteristics of digital images. In order to establish the individual frequency bands, filter kernels or a Fourier transformation can be used for example. The noise component can also be convoluted with a Gaussian filter (or with another lowpass filter), wherein the difference between the original and the filtered noise component represents the first frequency band. Then, with the filtered noise component the further process is exactly the same until the desired number of frequency bands is reached. The "rest" of the noise is then preferably to be found in the last frequency band. The number of frequency bands into which the noise component is decomposed and how wide these are (i.e. how wide the Gaussian filter is), should be set with the aid of the system attributes. A decomposition takes place especially preferably based on (such) a Laplace pyramid and will be explained in greater detail below.

The data points correspond to the information of the recording. In the case in which a reconstructed image is examined, the data points preferably correspond to the image points (pixels) of the image. In the case in which the recorded image comprises raw data, the data points correspond to image-relevant information of the raw data.

For a good decomposition knowledge of noise power spectrum of the input image to be expected should exist. This is given in particular for a plurality of medical imaging methods (e.g. CT, tomosynthesis or digital x-ray) or can be determined by a calibration if necessary. For example the characteristics of the noise (electronic noise: Gauss-distributed, photon noise: Poisson-distributed) are known for x-ray images and can either be derived directly from the recording parameters, measured (noise power spectrum) or calibrated. They can also be computed however when enough knowledge about the imaging system is available. This means that the statistical characteristics of the noise in the individual frequency bands is known.

Examination of the noise components (for a number of their image points/all image points) for (statistical) outlier image points of which the intensity lies outside a predetermined range of values and formation of moderate noise components by moderation of the values of the outlier image points established in the examination.

For example the statistics in the noise components (the "noise frequency bands") can be described via the standard deviation $\sigma$ and the average value. If a value in a noise frequency band now lies more than $3\sigma$ away from the average value, the value is highly likely to be an outlier, if a Gauss-type distribution is assumed. This threshold value can naturally also assume another value, likewise other parameters can be used to describe the noise statistics.

Subtraction of the moderated noise components from the recorded image.

This step is similar to the prior art wherein, unlike in the prior art, it is not the amount of noise that is taken away, but the moderated amount of noise (or the moderated noise components). The moderated noise components in this case can first be combined into a moderated amount of noise. They can however also be directly subtracted from the image individually. In practice a noise intensity value established for each pixel can simply be subtracted for each pixel from the intensity value (e.g. gray value) of the pixels, wherein a negative noise intensity value is naturally added in this context.

Thus the amount of noise is decomposed into a defined number of N noise components, which are examined afterwards in each data point or image point for statistical outliers, which are dealt with in a dedicated way (moderated). After moderation of the noise components the resulting moderated amount of noise is subtracted from the original image. The method described is thus intended to be applied to x-ray images after any given method for noise reduction. In such cases, it prevents relevant image contents being changed by the noise reduction method, by a bad choice of parameters for example.

Thus noise in dedicated frequency bands is considered within the framework of the invention.

An inventive apparatus for image noise reduction comprises the following components:

An (in particular medical) imaging system designed to produce a recorded image or a data interface for receiving a recorded image, e.g. a radiography system, mammography system (also tomosynthesis), fluoroscopy system or a computed tomography system, A noise reduction unit designed to establish an amount of noise of the recorded image, A decomposition unit designed to decompose the amount of noise into a predetermined number of N frequency-band-dependent noise components for N frequency bands, wherein the noise components comprise data points, which reproduce the noise at points in the recorded image for the frequency band concerned, A moderation unit designed to examine the noise components for outlier data points, the intensity of which lies outside a predetermined range of values and for formation of moderated noise components by moderation of the value of the outlier data points established in the noise components in the examination, Optionally a combination unit, which is designed to combine the moderated noise components into a moderated amount of noise, (before these are subtracted from the recorded image by the subsequent subtraction unit), and A subtraction unit designed to subtract the moderated noise components from the recorded image.

An inventive control facility for control of an imaging system, in particular a medical imaging system (in particular for x-ray images), preferably a radiography system, fluoroscopy system, mammography system or a computed tomography system, is designed for carrying out an embodiment of an inventive method and/or comprises an embodiment of an inventive apparatus.

An inventive imaging system, in particular a medical imaging system, preferably a radiography system, fluoroscopy system, mammography system or a computed tomography system, comprises an embodiment of an inventive control facility.

A main focus of an embodiment of the invention is on x-ray images of all kinds, in particular within the framework of computed tomography (CT), cone beam CT, classical (digital) radiography and fluoroscopy, mammography, tomosynthesis, and also on synthetic 2D images computed therefrom (for mammography and other radiographic applications such as for example lung imaging), DVT scanners for dental and HNO applications, line scanners (e.g. EOS system), bone density scanners (DXA) and other dual-energy x-ray images. These recording methods and recording devices are preferred methods or devices within the framework of the invention. In principle this invention is however also able to be applied within the framework of other imaging methods for which the noise characteristics are known.

A large part of the components specified above of the apparatus or of the control facility can be realized entirely or in part in the form of software modules in a processor of a corresponding apparatus or control facility. A largely software-based realization has the advantage that even apparatuses and control facilities previously used can be upgraded in a simple manner by a software update in order to work in an inventive way. To this extent the object is also achieved by a corresponding computer program product with a computer program, which is able to be loaded directly into a processing system or a memory facility of a control facility (e.g. of a computed tomography system), with program sections for carrying out all steps of the inventive method when the program is executed in the processing system or the control facility. Such a computer program product, as well as the computer program, can if necessary comprise additional elements, such as e.g. documentation and/or additional components including hardware components, such as e.g. hardware keys (dongles etc.) for using the software.

A computer-readable medium, e.g. a memory stick, a hard disk or any other transportable or permanently-installed data medium, on which the program sections of the computer program able to be read in and executed by a processing system or a processing unit of the control facility are stored can serve for transport to the processing system or to the control facility and/or for storage at or in the processing system or the control facility. For this purpose the processing unit can have one or more microprocessors or the like working together for example.

Further especially advantageous embodiments and developments of the invention emerge from the dependent claims and also from the description given below, wherein the claims of one claim category can also be developed in a similar way to the claims and parts of the description for another claim category and in particular individual features of different example embodiments or variants can be combined into new example embodiments or variants.

In accordance with a preferred method of an embodiment the recorded image has been produced via x-rays, in particular within the framework of a recording method of radiography, fluoroscopy, mammography, tomography or computed tomography. The recorded image is thus preferably an x-ray image or a CT image. Especially preferably the recorded image is based on a mammography recording and/or a tomosynthesis recording and is in particular a synthetic 2D image computed from a tomosynthesis recording or an image of an intermediate step of such a computation.

In accordance with a preferred method of an embodiment the amount of noise of the recorded image is established via a conventional image noise reduction algorithm. A preferred conventional image noise reduction algorithm is based on BM3D and/or IRIS (see above) and/or on artificial intelligence. In this method the recorded image is preferably subdivided into the amount of noise and a component of conventional image information ("image information", since this represents a denoised image, "conventional", since this corresponds to the prior art and is only optimized by the method). The conventional image information in this case represents the denoised image in accordance with the image noise reduction algorithm used and can be used together with the denoised image in accordance with the invention to improve the image noise reduction algorithm, e.g. for training an algorithm capable of learning.

In accordance with a preferred method of an embodiment the decomposition of the amount of noise is done based on a Laplacian pyramid. A Gaussian or Laplacian pyramid, sometimes also called a Burt-Adelson pyramid, is a digital signal processing algorithm and is well known in the prior art for frequency-dependent decomposition of images.

As an alternative the decomposition of the amount of noise can also be done based on a Fast-Fourier transformation or a wavelet transformation. These transformations are known to the person skilled in the art.

In accordance with a preferred method of an embodiment, the data points of the noise components are image points of an image or they can be reconstructed to form image points of an image, which represents the noise component concerned for the frequency band concerned.

In accordance with a preferred method of an embodiment the examination of the noise components for outlier data points and the formation of moderated noise components is done by a moderation function. This moderation function moderates the values of those data points that lie outside a predetermined range of values and preferably leaves the values of the data points within the range of values unchanged. This moderation preferably takes place such that values outside a value interval are changed so that they lie closer to the average value of the value interval. It is preferred in this case that the values of those data points that lie outside a predetermined range of values are changed by the moderation function so that they lie within the predetermined range of values, preferably in which the values of the data points concerned are set to the limits of the predetermined range of values or, with an increasing distance from the predetermined range of values, are adapted to be closer to the average value of the predetermined range of values. For example values that lie above or below a threshold value can be set to this threshold value (which would represent the moderation) or be moderated so that, as their distance from the threshold value increases, they are pulled back ever closer towards the average value M.

In accordance with a preferred method of an embodiment a combination of the moderated noise components with the outlier data points dealt with to form a resulting amount of noise is done before the subtraction of the moderated noise components from the recorded image.

In general it can be about the outliers that, in a predetermined statistical distribution (e.g. Gauss or Poisson), these represent statistical outliers and are changed so that they "fit" the distribution again.

If Fn is a moderation function, An a noise component and Mn a moderated noise component for the nth frequency band, then preferably: Mn=Fn(An) applies.

It is generally preferred that the frequency bands of the noise components taken together produce a contiguous frequency range. Or the noise component in its entirety should be divided up so that there are no non-allocated noise components that lie at frequencies between two noise components used for the method. Frequencies at which no noise components lie do not necessarily have to be considered here.

In accordance with a preferred method of an embodiment, as a part of recording the image, a noise behavior of equipment used for recording is measured and/or calibrated. It is preferred in this case that the moderation function depends on the measured noise behavior and/or the image recording takes place after the calibration. "Calibration" in this case means a noise-related calibration, which takes account of or evaluates the nature of the noise. For example the components of Gaussian noise or Poisson noise, which are mathematically well known, are established via the calibration. The more precisely the noise components are known, the better the amount of noise in noise components is able to be decomposed and moderation functions established with which outliers can be moderated. The technique of calibration is known to the person skilled in the art.

In accordance with a preferred method of an embodiment the amount of noise is preferably decomposed into more than two noise components, preferably into three noise components. Naturally it is possible for more noise components to be used, however it has been shown that, with a suitable choice of noise bands, not more than 3 are needed in order to achieve a good result. Preferably those noise components with the highest frequency bands are chosen and especially preferably a noise component comprises the "rest" of the amount of noise, so that the amount of noise is contained fully in the noise components.

Preferably components of the invention are present as a "Cloud service". Such a Cloud service serves to process data, in particular via an artificial intelligence, but can also be a service based on conventional algorithms or a service in which an evaluation by human beings takes place in the background. In general a Cloud service (also referred to below as a "Cloud" for short) is an IT infrastructure in which for example storage space or processing power and/or application software is made available via a network. Communication between the user and the Cloud takes place in such cases via data interfaces and/or data transmission protocols. In the present example it is especially preferred for the Cloud service to make available both processing power and also application software.

Within the framework of a preferred method of an embodiment there is a provision of data via the network to the Cloud service. This comprises a processing system, e.g. a computer cluster, which as a rule does not include the user's local computer. This Cloud can in particular be made available by the (medical) facility, which also makes available the (medical) systems. For example the data of an image recording is sent via an RIS (Radiology Information System) or PACS to a (remote) processor system (the Cloud). Preferably the processing system of the Cloud, the network and also the (medical) system represent a cluster in the data processing sense. The method can be realized in this case by a command constellation in the network. The data computed in the Cloud ("result data") is later sent back via the network to the user's local computer.

The advantage of at least one embodiment of the invention is that the application of a frequency-based method with specific regard to AI-based methods delivers a high level of resulting faithful images, since in particular the risk of structures being removed, emphasized or added in by the noise reduction is curbed. The method is especially advantageous for noise reduction algorithms of which the performance is greatly determined by image content that cannot be foreseen, i.e. AI-based methods for example, although they have been trained and tested on sufficiently large but finite datasets.

In the following explanations it is assumed that the imaging equipment involves a computed tomography system. Basically however the method is also able to be used in other imaging equipment within medical engineering and outside of it.

Figure 1:
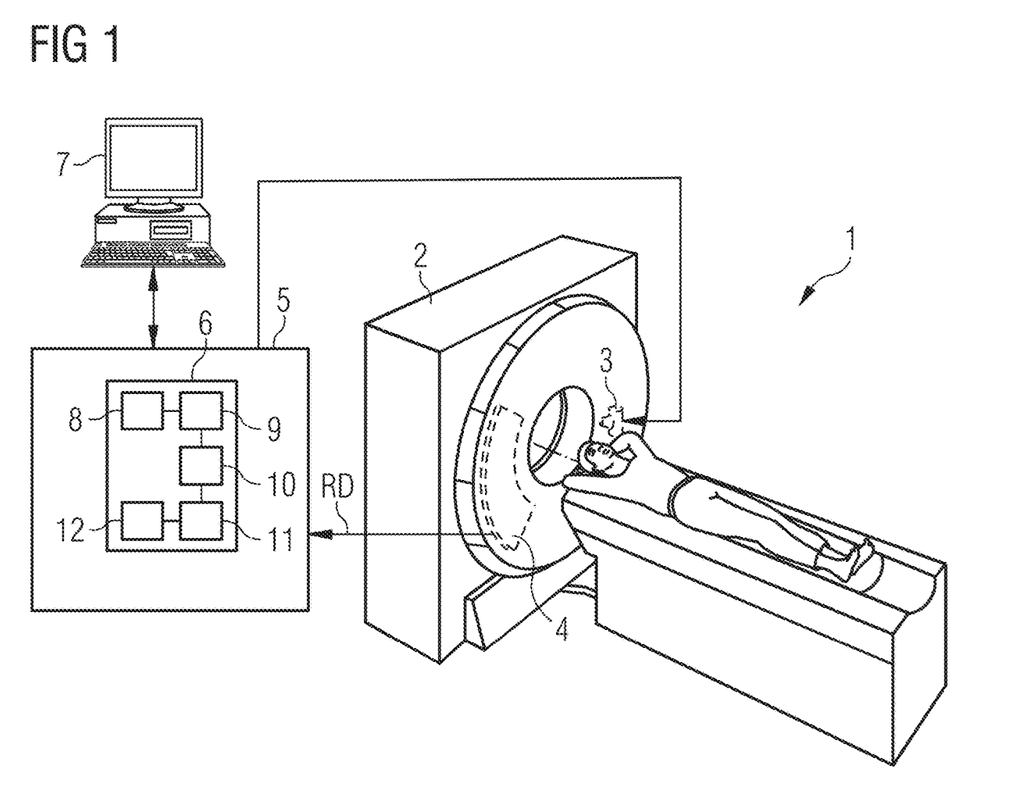
FIG. 1 shows a rough schematic diagram of a computed tomography system with an example embodiment of a control facility with an inventive apparatus for carrying out an example embodiment of the method.

FIG. 1 shows a rough schematic of a computed tomography system 1 with a control facility 5 for carrying out an embodiment of the inventive method. In the usual way the computed tomography system 1 has a scanner 2 with a gantry, in which an x-ray source 3 rotates, which in each case irradiates a patient P who is pushed into a measuring chamber of the gantry via a couch, so that the radiation strikes a detector 4 lying opposite the x-ray source 3 in each case. It is expressly pointed out that this example embodiment only involves an example of a CT and the invention can also be used on any given CT constructions, for example with annular fixed x-ray detector and/or a number of x-ray sources.

Likewise in the control facility 5 only the components that are of significance for the explanation of the invention are shown. Basically these types of CT systems and associated control facilities are known to the person skilled in the art and therefore do not need to be explained in detail. A core component of the control facility 5 here is a processor, on which different components, here in particular an embodiment of the inventive apparatus 6, are realized in the form of software modules. The control facility 5 in this case has an interface, to which a terminal 7 is connected, via which an operator can operate the control facility 5 and thus can operate the computed tomography system 1.

The apparatus 6 in the control facility 5 comprises a noise reduction unit 8, a decomposition unit 9, a moderation unit 10, a combination unit 11 and a subtraction unit 12, which will be described below in greater detail together with the execution sequence of the method.

Figure 2:
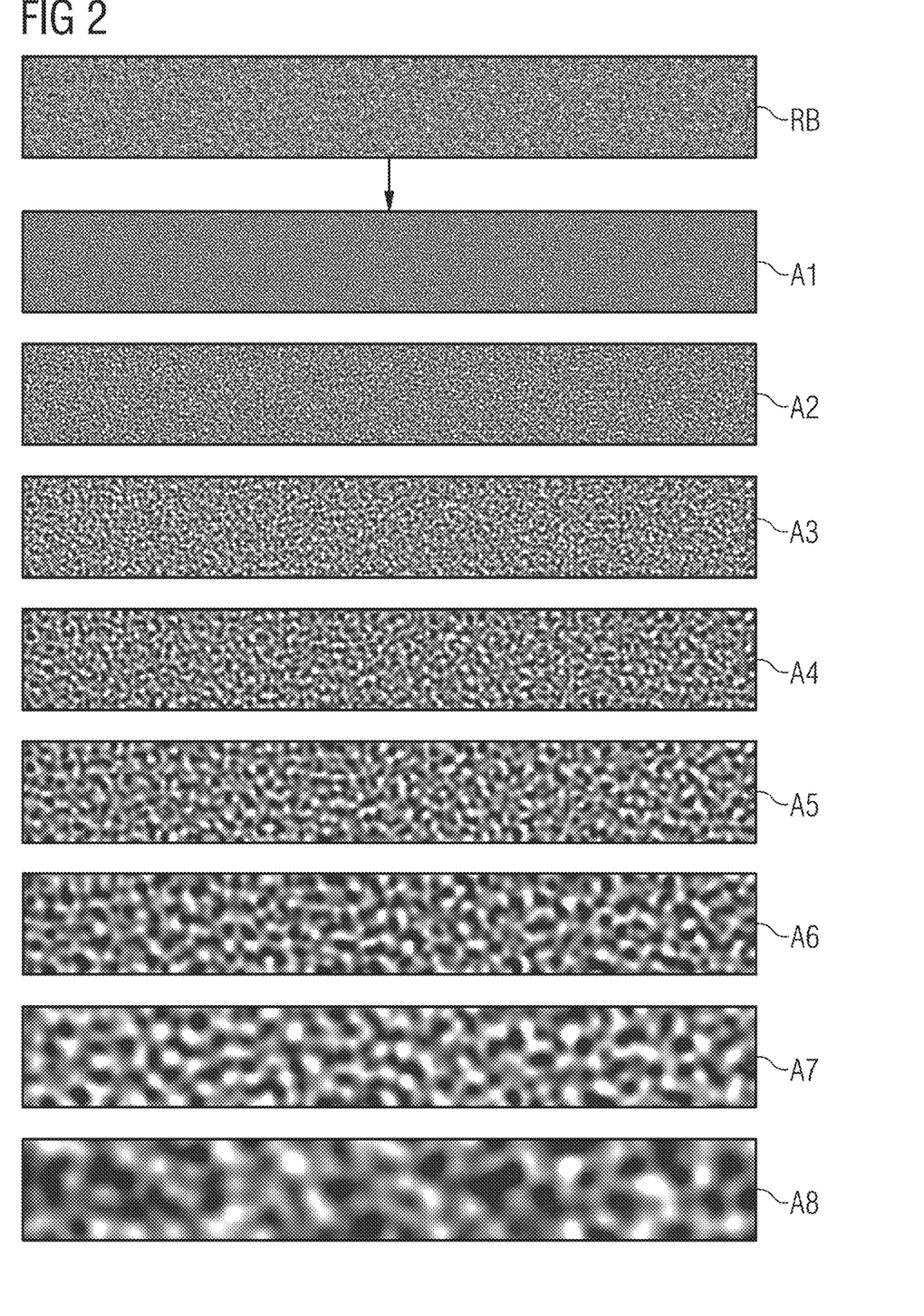
FIG. 2 shows the nature of the frequency-dependent noise components.

FIG. 2 illustrates the nature of the frequency-dependent noise components A1, A2, A3, A4, A5, A6, A7, A8. An amount of noise RB (noise of the entire recorded image B, see e.g. FIG. 6) is decomposed into 8 frequency-dependent noise components A1, A2, A3, A4, A5, A6, A7, A8. For improved clarity the intensity is adapted to the individual noise components A1, A2, A3, A4, A5, A6, A7, A8. The main noise is contained in the first three noise components A1, A2, A3.

Figure 3:
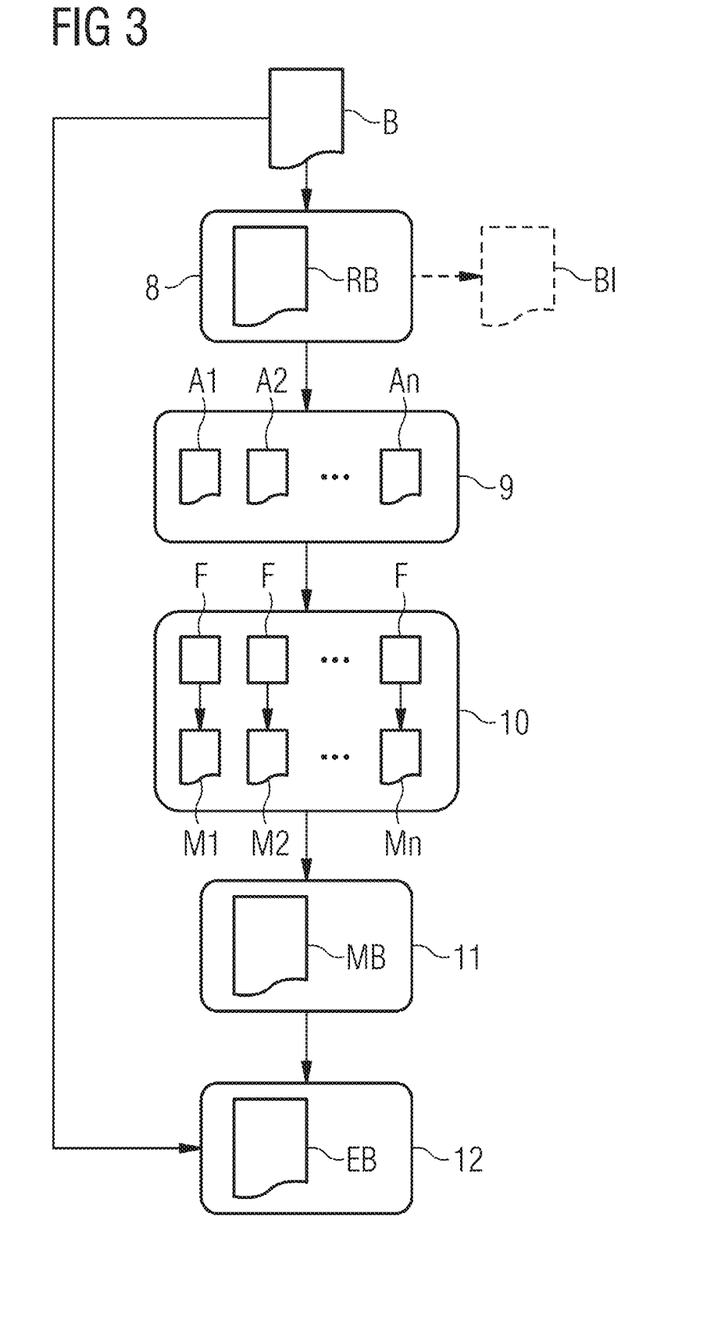
FIG. 3 shows a flowchart for the possible execution sequence of an example embodiment of an inventive method.

FIG. 3 shows a flowchart for a possible execution sequence of an embodiment of an inventive method. First of all a recorded image B is produced. This recorded image B will be more or less affected by noise and is to be denoised by way of an embodiment of the inventive method.

To this end the amount of noise RB of the recorded image B is first established in a noise reduction unit 8. This will naturally not be the true noise component, but merely that component which the (conventional) algorithm used for this purpose for noise reduction estimates as the noise component. In addition the conventional image information BI (an image SdT denoised with the algorithm, see FIG. 6) can be established, which is shown here by a dashed outline. It should be noted that a denoising algorithm as a rule delivers the conventional image information BI (i.e. a conventional noise-reduced image) and the amount of noise RB is produced in this case by a subtraction of the conventional image information BI from the recorded image B.

The amount of noise RB established is then decomposed in the decomposition unit 9 into a plurality of frequency-dependent noise components A1, A2, An. The decomposition can be done here based upon a Laplace pyramid for example. In this case the noise components A1, A2, An comprise image points (or data points), which reproduce noise at points of the recorded image for the frequency band concerned.

These noise components A1, A2, An are now examined in a moderation unit 10 for statistical outlier image points, the intensities of which lie outside a predetermined range of values. This can be done via a moderation function F, which can be used at the same time for the formation of moderated noise components M1, M2, Mn (see FIG. 4 or 5), by the moderation function F being used to moderate the values of the outlier image points A1, A2, An in the noise components established in the examination.

The modulation function F in this particular example is chosen to be the same in each case. Typically however it will be chosen individually (different) for each frequency band. The threshold value which specifies the value from which moderation is to take place can in this case also have a different value in each frequency band.

In a subsequent combination unit 11 the moderated noise components M1, M2, Mn are combined into a moderated amount of noise MB. This step is optional, since the method can also work with the individual moderated noise components M1, M2, Mn.

Lastly the moderated noise components M1, M2, Mn, in the form of the moderated amount of noise MB, are subtracted by a subtraction unit 12 from the recorded image B and thus the denoised image EB created.

In a preferred moderation function F values with an intensity within the threshold value (e.g. with a deviation of less than three times the standard deviation) are left as they are. Values that lie outside are outliers and are set to a pre-defined threshold value. Two preferred graphs for moderation functions F1, F2 are presented below.

Figure 4:
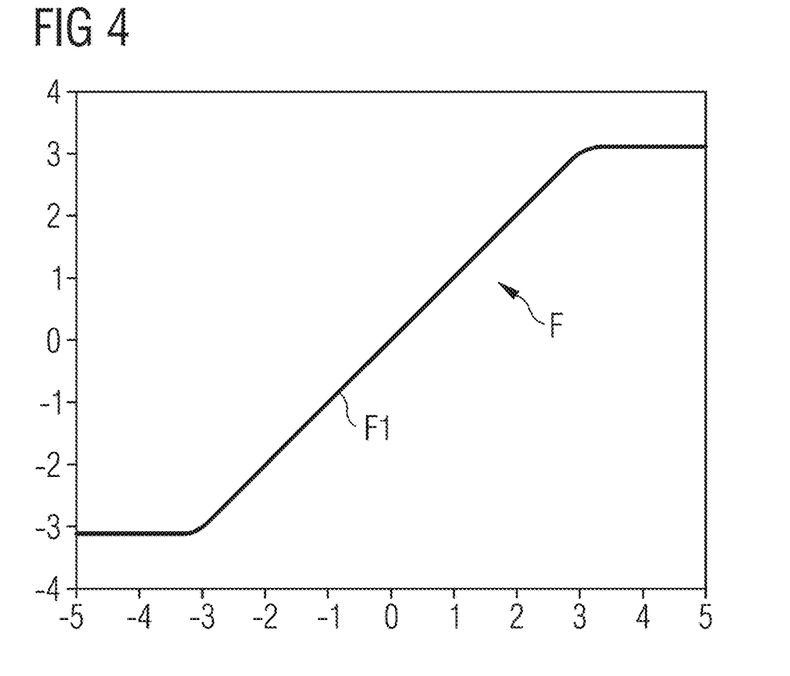
FIG. 4 shows a preferred moderation function graph.

FIG. 4 shows a preferred moderation function graph F1, which has the example threshold value of 3, which corresponds to a deviation by three times the standard deviation. The X axis in this graph reflects the pixel value in the noise component A1, A2, An, the Y axis the pixel value in the moderated noise component M1, M2, Mn. If this function is applied to the image points of an amount of noise A1, A2, An, all values of points with values either side of three times the standard deviation (greater or less) are set to the corresponding three times the standard deviation (3 or −3). In order to avoid a kink in the function there can still be a small area in which it continuously tapers.

Figure 5:
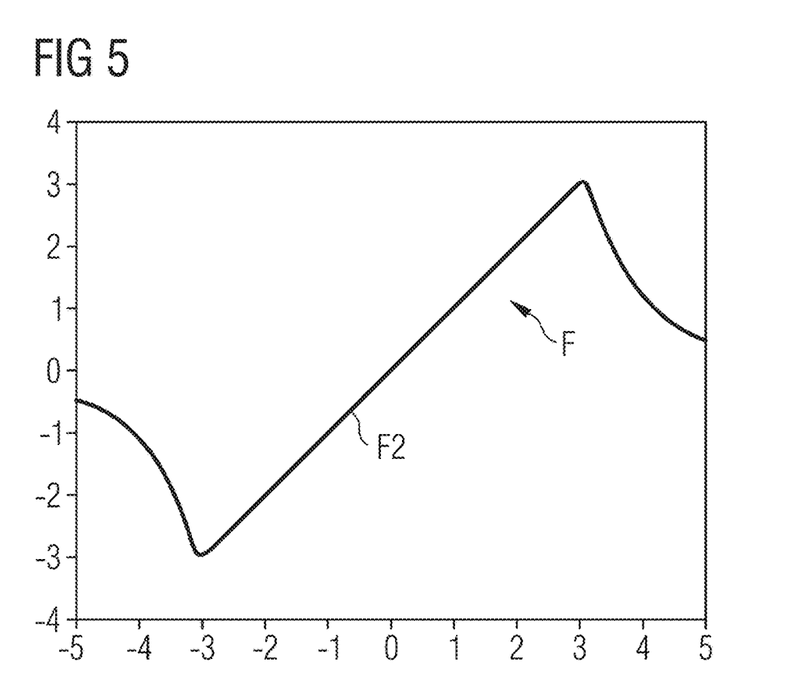
FIG. 5 shows a further preferred moderation function graph.

FIG. 5 shows a further preferred moderation function graph F2, which not only restricts the amplitude of outliers but increasingly suppresses it as the deviation increases. Here too the threshold value equals 3, as in FIG. 4.

Figure 6:
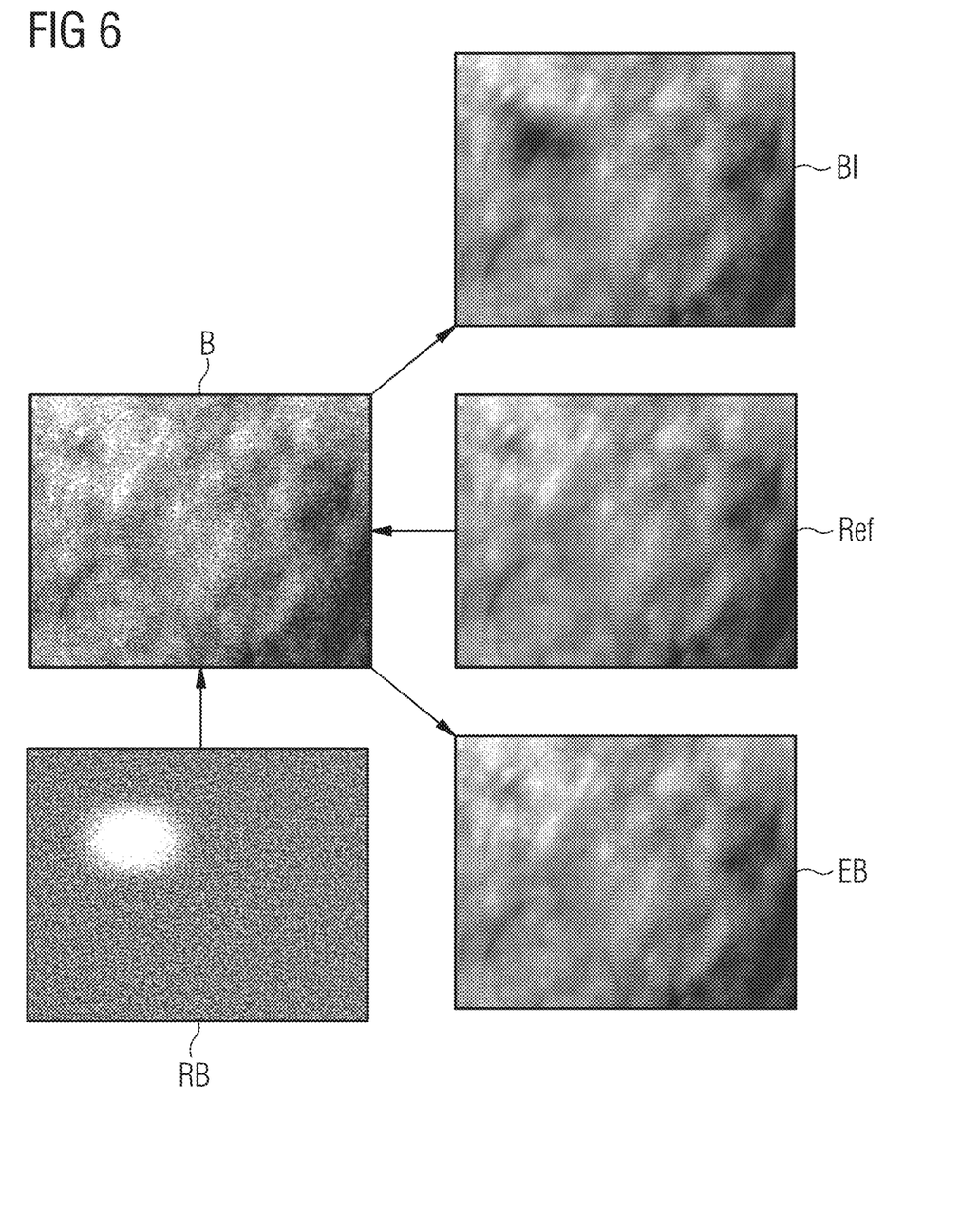
FIG. 6 shows a comparison of a result of an example embodiment of the invention with the prior art.

FIG. 6 shows a comparison of a result (denoised image EB) of an embodiment of the invention with an example of a denoised image according to the prior art (for better visualization incorrect behavior has been simulated here). On the right in the middle can be seen a reference image, which shows a mammography image. This image only comprises a very slight noise component.

This reference image Ref has now been provided with an amount of noise RB, which is shown on the left at the bottom. The resulting noisy image is now the original image here, i.e. the noisy recorded image B, and is shown on the left in the middle.

This recorded image is now t. Once by way of a conventional method for image noise reduction and once with an embodiment of the inventive method. The denoised image in accordance with the prior art (the conventional image information BI according to FIG. 3) is shown on the right at the top and has a clearly visible shadow in the top left corner, which could be incorrectly interpreted as a structure. By contrast the denoised image EB on the right at the bottom, in which the noise reduction was undertaken according to the inventive method, corresponds more to the reference image Ref.

Figure 7:
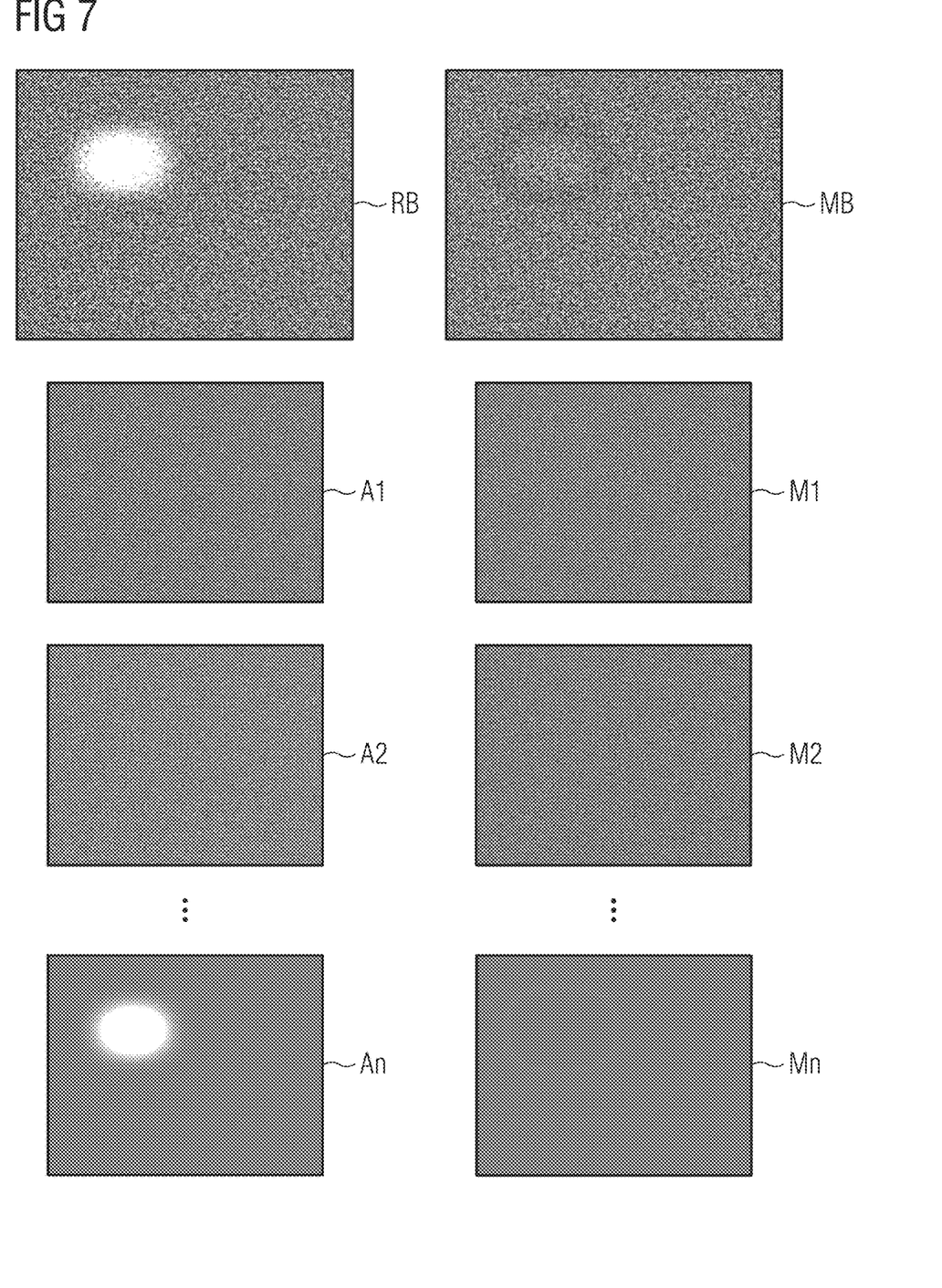
FIG. 7 shows noise components of the amount of noise of FIG. 6.

In FIG. 7 noise components A1, A2, An of the amount of noise RB of FIG. 6 are shown and it is explained how the incorrect shadow in the conventional image information BI in the example shown in FIG. 6 is removed in accordance with the inventive method. The amount of noise (shown on the left at the top) from FIG. 6 is decomposed into n noise components A1, A2, An, of which those of the first two frequency bands and of the nth frequency band are shown on the left. In the first two noise components A1, A2 there are few outliers visible or none at all, however in the nth frequency band the bright outlier area that causes the shadow in the conventional image information in FIG. 6 is plainly visible. On the right, as well as the noise components A1, A2, An, the modulated noise components M1, M2, Mn are shown. Although the first two modulated noise components M1, M2 still strongly resemble the first two noise components A1, A2 (on account of the few outliers), in the last modulated noise component Mn compared to the last noise component An the bright outlier area has been modulated, e.g. via the function from FIG. 4.

Shown at the top on the right is the resulting modulated amount of noise MB, which is produced from the modulated noise components M1, M2, Mn. If this modulated amount of noise MB is used, the denoised image EB in FIG. 6 no longer exhibits the shadow of the conventional image information BI.

In conclusion it is pointed out once again that the method described above in detail and also the computed tomography system 1 shown merely involve example embodiments, which can be modified by the person skilled in the art in a wide diversity of ways without departing from the field of the invention. Furthermore the use of the indefinite article "a" or "an" does not exclude the features concerned also being able to be present multiple times. Likewise the terms "unit" and "module" do not exclude the components concerned consisting of a number of interacting subcomponents, which where necessary can also be spatially distributed.

Although the invention has been illustrated and described in detail by the preferred embodiments, the invention is not limited by the disclosed examples and other variations can be derived herefrom by the person skilled in the art without departing from the scope of protection of the invention.

Even if not explicitly stated, individual example embodiments, or individual sub-aspects or features of these example embodiments, can be combined with, or substituted for, one other, if this is practical and within the meaning of the invention, without departing from the present invention. Without being stated explicitly, advantages of the invention that are described with reference to one example embodiment also apply to other example embodiments, where transferable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112 (f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for image noise reduction, comprising:
producing a recorded image;
establishing an amount of noise of the recorded image;
decomposing the amount of noise into a number of N frequency-dependent noise components for N frequency bands, each of the N frequency-dependent noise components including data points, the data points reproducing the amount of noise of the recorded image for a respective N frequency band;
examining the number of N frequency-dependent noise components for outlier data points, each of the outlier data points having an intensity outside of a range of values;
forming moderated noise components by moderation of values of the outlier data points; and
subtracting the moderated noise components from the recorded image.

2. The method of claim 1, wherein the recorded image has been produced via x-rays.

3. The method of claim 1, wherein the amount of noise of the recorded image is established, in the establishing, via an image noise reduction algorithm.

4. The method of claim 1, wherein the decomposing of the amount of noise is carried out based upon a Laplace pyramid, a Fast-Fourier transformation, or a wavelet transformation.

5. The method of claim 1, wherein the data points are image points of an image or reconstructable to image points of an image, each image point representing a respective noise component for the respective N frequency band.

6. The method of claim 1, wherein the examining of the number of N frequency-dependent noise components for outlier data points and the forming of the moderated noise components is carried out by a moderation function, the moderation function moderating the values of the outlier data points and leaving values of the data points within the range of values unchanged.

7. The method of claim 1, wherein, before the subtracting of the moderated noise components from the recorded image, the moderated noise components are combined to form one moderated amount of noise, the N frequency bands, taken together, producing a contiguous frequency range.

8. The method of claim 1, wherein producing the recorded image further includes at least one of
measuring a noise behavior of equipment used for recording, wherein the moderating depends on the noise behavior measured, and
calibrating a noise behavior of the equipment used for recording, wherein the calibrating takes place before a recording of an image.

9. The method of claim 1, wherein the amount of noise is decomposed during the decomposing into more than two noise components.

10. An apparatus for image noise reduction, comprising:
at least one of an imaging system designed to produce a recorded image and a data interface to receive a recorded image;
a noise reduction unit to establish an amount of noise of the recorded image;
a decomposition unit to decompose the amount of noise into a number of N frequency-dependent noise components for N frequency bands, each of the N frequency-dependent noise components including data points, the data points reproducing the amount of noise of the recorded image for a respective N frequency band;
a moderation unit to examine the number of N frequency-dependent noise components for outlier data points each of the outlier data points having an intensity outside of a range of values, and to form moderated noise components by moderation of values of the outlier data points; and
a subtraction unit to subtract the moderated noise components from the recorded image.

11. The apparatus of claim 10, further comprising:
a combination unit, to combine the moderated noise components into one moderated amount of noise, the moderated noise components being combined before the moderated noise components are subtracted from the recorded image.

12. A control facility for controlling an imaging system, comprising:
the apparatus of claim 10.

13. An imaging system, comprising the control facility of claim 12.

14. A non-transitory computer program product storing a computer program, directly loadable into a memory facility of a control facility, including program sections for carrying out the method of claim 1 when the computer program is executed in the control facility.

15. A non-transitory computer-readable medium, storing program sections readable in and executable by a processor, to carry out the method of claim 1 when the program sections are executed by the processor.

16. The method of claim 2, wherein the recorded image has been produced via x-rays within a framework of a recording method of radiography, fluoroscopy, mammography, tomography, or computed tomography.

17. The method of claim 2, wherein the recorded image is based on at least one of a mammography recording and a tomosynthesis recording.

18. The method of claim 2, wherein the recorded image is a synthetic 2D-image computed from a tomosynthesis recording or an image of an intermediate step of a computation.

19. The method of claim 3, wherein image noise reduction algorithm is based on at least one of BM3D, an iterative CT image filter for noise reduction, and artificial intelligence.

20. The method of claim 2, wherein the decomposing of the amount of noise is carried out based upon a Laplace pyramid, a Fast-Fourier transformation, or a wavelet transformation.

21. The method of claim 2, wherein the data points are image points of an image or reconstructable to image points of an image, each image point representing a respective noise component for the respective N frequency band.

22. The method of claim 3, wherein the recorded image is subdivided into the amount of noise and a component of image information.

23. The method of claim 6, wherein the values of the outlier data points are changed by the moderation function, the changed values being inside the range of values.

24. The method of claim 23, wherein the values of the outlier data points are set to limits of the range of values, or, as a distance of the values of the outlier data points from the range of values increases, the values of the outlier data points are changed to be closer to an average value of the range of values.

25. The method of claim 9, wherein the amount of noise is decomposed during the decomposing into three noise components.

26. The method of claim 9, wherein noise components with relatively highest frequency bands are chosen.

27. A control facility for controlling an imaging system, comprising:
the apparatus of claim 11.

28. The imaging system of claim 13, wherein the imaging system is at least one of a radiography system, a fluoroscopy system, a mammography system, a tomography system or a computed tomography system.

29. The method of claim 1, wherein the range of values is defined by values within a predetermined number of standard deviations away from an average value of the noise for a respective N frequency-dependent noise component, the intensity of each outlier data point having a deviation greater than the predetermined number of standard deviations.

* * * * *